(12) United States Patent
Ning et al.

(10) Patent No.: US 7,643,605 B2
(45) Date of Patent: Jan. 5, 2010

(54) METHOD AND APPARATUS FOR CONE BEAM CT DYNAMIC IMAGING

(75) Inventors: Ruola Ning, Fairport, NY (US); Dong Yang, Rochester, NY (US)

(73) Assignee: University of Rochester, Rochester, NY (US)

( * ) Notice: Subject to any disclaimer, the term of this patent is extended or adjusted under 35 U.S.C. 154(b) by 0 days.

(21) Appl. No.: 11/711,155

(22) Filed: Feb. 27, 2007

(65) Prior Publication Data

US 2007/0253528 A1    Nov. 1, 2007

Related U.S. Application Data

(60) Provisional application No. 60/776,666, filed on Feb. 27, 2006.

(51) Int. Cl.
*A61B 6/03* (2006.01)
(52) U.S. Cl. .......................... 378/4; 378/901
(58) Field of Classification Search ............ 378/4, 378/901; 382/128–131
See application file for complete search history.

(56) References Cited

U.S. PATENT DOCUMENTS

| | | | |
|---|---|---|---|
| 3,973,126 A | 8/1976 | Redington et al. | |
| 4,015,836 A | 4/1977 | Redington et al. | |
| 5,170,439 A | 12/1992 | Zeng et al. | |
| 5,526,394 A | 6/1996 | Siczek et al. | |
| 5,602,891 A | 2/1997 | Pearlman | |
| 5,999,587 A | 12/1999 | Ning et al. | |
| 6,075,836 A | 6/2000 | Ning | |
| 6,282,256 B1 * | 8/2001 | Grass et al. | 378/15 |
| 6,298,110 B1 | 10/2001 | Ning | |
| 6,298,114 B1 | 10/2001 | Yoda et al | |
| 6,477,221 B1 | 11/2002 | Ning | |
| 6,480,565 B1 | 11/2002 | Ning | |
| 6,504,892 B1 | 1/2003 | Ning | |
| 6,618,466 B1 | 9/2003 | Ning | |
| 6,987,831 B2 | 1/2006 | Ning | |
| 7,245,755 B1 * | 7/2007 | Pan et al. | 382/131 |
| 2003/0073893 A1 * | 4/2003 | Hsieh | 600/407 |

(Continued)

FOREIGN PATENT DOCUMENTS

WO    WO-93/17620    9/1993

(Continued)

OTHER PUBLICATIONS

Tang et al., A three-dimensional weighted cone beam filtered backprojection (CB-FBP) algorithm for image reconstruction in volumetric CT under a circular source trajectory, Aug. 3, 2005, Physics in Medicine and Biology, vol. 50, pp. 3889-3906.*

(Continued)

*Primary Examiner*—Chih-Cheng G Kao
*Assistant Examiner*—John M Corbett
(74) *Attorney, Agent, or Firm*—Blank Rome LLP

(57) ABSTRACT

A cone-beam scanning system scans along a half circle. The reconstruction uses a weighting function which decreases for rows farther from the scan plane to take the redundancy of the projection data into account. Another embodiment uses a circle plus sparse helical scan geometry. Image data can be taken in real time.

10 Claims, 5 Drawing Sheets

U.S. PATENT DOCUMENTS

2004/0081273 A1* 4/2004 Ning .................. 378/37
2006/0094950 A1    5/2006 Ning

FOREIGN PATENT DOCUMENTS

WO    WO-99/01066    1/1999

OTHER PUBLICATIONS

Hu, A New Cone Beam Reconstruction Algorithm for the Circular Orbit, 1995, IEEE Nuclear Science Symposium and Medical Imaging Conference 1994 Conference Record, vol. 3, pp. 1261-1265.*

Kornmesser et al., Fast Feldkamp-reconstruction for real-time reconstruction using C-arm systems, 2002, Proceedings of the 16th International Congress and Exposition Computer Assisted Radiology and Surgery (CARS 2002), ISBN 3-540-43655-3, pp. 430-434.*

Hu, Exact Regional Reconstruction of Longitudinally-Unbounded Objects Using the Circle-and Line Cone Beam Tomographic System, 1997, SPIE vol. 441, pp. 441-444.*

Zhao et al., Feldkamp-Type Cone-Beam Tomography in the Wavelet Framework, 2000, IEEE Transactions on Medical Imaging, vol. 19, No. 9, pp. 922-929.*

Yang et al., Modified FDK half-scan (MFDKHS) scheme on flat panel detector-based cone-beam CT, Apr. 2005, SPIE vol. 5745, Proceedings of Medical Imaging 2005: Physics in Imaging held Feb. 13, 2005, pp. 1030-1037.*

Yang et al., Implementation & Evaluation of the Half-Scan Scheme Based on CBCT (Cone-Beam CT) system, 2004, SPIE vol. 5368, Proceedings of Medical Imaging 2004: Physics, pp. 542-551.*

Tang et al., A Three-dimensional Weighted Cone Beam Filtered Back Projection (CB-FBP) Algorithm for Image Reconstruction in a Volumetric CT Under a Circular Source Trajectory, Physics in Medicine and Biology, Aug 3, 2005, vol. 50, pp. 3889-3905.

Hu, H., "A New Cone Beam Reconstruction Algorithm for the Circular Orbit," IEEE Nuclear Science Symposium and Medical Imaging Conference 1994 conference Record, 1995, vol. 3, pp. 1261-1265.

Kornmesser at al., "Fast Feldkamp-reconstruction for Real-time Reconstruction Using C-arm Systems," Proceedings of the 16th International Congress and Exposition on Computer Assisted Radiology and Surgery (CARS 2002), 2002, ISBN 3-540-43655-3, pp. 430-434.

Yu et al., Application of Asymmetric Cone-beam CT in Radiotherapy, Oct. 22, 2004, IEEE Nuclear Science Symposium Conference Record 2004, vol. 5, pp. 3249-3252.

Zhao et al., "Feldkamp-Type Cone-Beam Tomography in the Wavelet Framework," Sep. 9, 2000, IEEE Transactions on Medical Imaging, vol. 19, No. 9, pp. 922-929.

Chang, C. H. Joseph, et al., "Computed Tomography of the Breast", Radiology, vol. 124, No. 3, pp. 827-829, Sep. 1977.

Chang, C. H. Joseph, et al., "Computed Tomographic Evaluation of the Breast," Am J Roentgenol 131:459-484, Sep. 1978.

Chang, C. H. Joseph, et al., "Computed Tomography in Detection and Diagnosis of Breast Cancer," Cancer August Supplement 1980, vol. 46, pp. 939-946.

Anderson, William H., et al, "An Interactive Computer Graphics System for the Computed Tomographic Breast Scanner (CT/M)," CH 1515—6/79/0000.75, 1979 IEEE, pp, 350-354.

Feldkamp, L. A., et al, "Practical Cone-Beam Algorithm," J. Opt. Soc. Am. A/vol. 1, No. 6/Jun. 1984, pp. 612-619.

* cited by examiner

METHOD AND APPARATUS FOR CONE BEAM CT DYNAMIC IMAGING

REFERENCE TO RELATED APPLICATION

The present application claims the benefit of U.S. Provisional Patent Application No. 60/776,666, filed Feb. 27, 2006, whose disclosure is hereby incorporated by reference in its entirety into the present disclosure.

STATEMENT OF GOVERNMENT INTEREST

The work leading up to the present invention was supported by NIH Grants 8 R01 EB002775, R01 9 HL078181, and 4 R33 CA94300. The government has certain rights in the invention.

FIELD OF THE INVENTION

The present invention is directed to imaging and more specifically to a half-scan imaging technique using a weighting function to increase temporal resolution.

DESCRIPTION OF RELATED ART

The use of the half-scan method in cone beam CT has been a hot topic in recent years owing to the resultant improvement in temporal resolution. There are currently several different types of cone beam half-scan schemes, such as FDK-based, cone beam filtered-backprojection-based (CBFBP), and Grangeat-based. Each scheme uses planar scanning trajectories (circular or non-circular) to conduct the half-scan scheme. Theoretically, a circular half scan can acquire approximately the same information in the radon domain as a circular full-scan in terms of the first derivative radial data, as long as the reconstructed object is within a certain size based on the derivation of the Grangeat formula. Even in the circular half-scanning range, redundancy still exists. The Grangeat-type half-scan (GHS) maps the spatial projection data into the first derivative radial data and weights them in the radon domain. After adding missing data through linear interpolation/extrapolation in the shadow zone of the radon domain where a circular scan can't access, a 3-D radon inverse formula is used to get the reconstructed image.

Current FDK-type half-scan (FDKHSFW) schemes for cone beam CT use Parker's or other weighting coefficients based on fan beam geometry where same weighting coefficients are applied to all detector rows. The CBFBP algorithm manipulates the redundant projection data in the radon domain, does the half-scan reconstruction in the structure of filtered backprojection (FBP) and achieves almost the same performance as FDKHSFW. The Grangeat-type half-scan scheme outperforms the FDK-type half-scan scheme in the correction of the off-scanning plane attenuation coefficient drop when the shadow zone is filled with the linear interpolated data. However, the spatial resolution of the reconstructed images from GHS is inferior to that of FDKHSFW because data interpolation is less involved in FDK than in GHS. Furthermore, GHS cannot handle the truncated data in the longitudinal direction. The CBFBP-related half-scan and FDKHSFW showed obvious attenuation coefficient drop artifacts in the position of the reconstructed image farthest away from Z=0, where Z is the rotation axis. This artifact is undesirable in practice.

SUMMARY OF THE INVENTION

It is an object of the invention to correct the drop problem to a certain degree.

It is another object of the invention to do so while maintaining spatial resolution.

To achieve the above and other objects, the present invention is directed to a FDK half scan scheme with a new weighting function that fits the cone beam geometry (FDKHSCW) where the weighting function is cone beam geometry dependent. The FDK half-scan algorithm with the new cone beam weighting function is described. A computer simulation has been conducted, and the FDKHSCW has been evaluated in comparison to FDKFS and FDKHSFW.

A new cone beam weighting scheme has been heuristically proposed for the FDK-based circular half scan reconstruction (FDKHSCW) to correct the density drop artifact to a certain degree along the rotation axis inherited with original FDK algorithm for large cone angle. Computer simulation on the Shepp-Logan phantom with and without noise showed an improvement when using the FDKHSCW over FDKFS and FDKHSFW in terms of the attenuation coefficient drop when the cone angle is large while maintaining the same visual image quality. FDKHSCW needs additional cone-beam weighting before filtering and only uses a scanning range of $[\beta, 180+\beta+2\Delta]$, where $\beta$ is the starting projection angle of the x-ray, and $\Delta$ is half of the full fan angle; both of them are defined in the scanning plane. As soon as the starting angle is determined, each projection image can be processed (cone-beam weighting for half scan, pixel weighting inherited by FDK, and filtering). So, it will take less time to reconstruct an object in comparison to the full scan scheme, a very desirable feature in practice. Here the half scan is defined as 180° plus cone angle of the scan geometry. In addition, the half-scan scheme provides a flexibility to choose any starting point for reconstruction as long as the scanning range is guaranteed, another preferable feature for cone beam CT dynamic imaging. If a full circle scan is performed, to increase temporal resolution of the system and cone beam CT reconstruction, a multiple of half scan reconstructions can be performed from the full circle scan by choosing the different starting point. Therefore it is another objective of the invention that using the half scan algorithm to reconstruct a multiple of half scan reconstructions from a circle or multiple circle scan projection images of an object to increase temporal resolution for cone beam CT dynamic imaging scan.

Based on the idea proposed by Silver (M. D. Silver, "A method for including redundant data in computed tomography," *Med. Phys.* 27, 773-774 (2000)), we can even conduct an extended half-scan scheme by making the scanning range larger than $180+2\Delta$ applying this new cone beam weighting function for better noise characteristic.

The circular cone-beam half-scan weighting scheme works better for low contrast objects. We can see from our simulation on Shepp-Logan phantom that the largest compensation is within 0.03 in terms of attenuation coefficient. We expect that FDKHSCW can show improvement in terms of intensity drop in high-contrast phantoms, like a Defrise disk phantom. Yet it is more promising with low-contrast phantoms.

Other proposed modified FDK methods called T-FDK and FDK-SLANT, also corrected the attenuation coefficient drop to some extent along the rotation axis inherited in FDK with a larger cone angle. There is a difference between these methods and FDKHSCW. Although the results of these methods showed similar correction to FDKHSCW, FDK-SLANT and T-FDK need to be parallel rebinned from cone beam data. That means the filtering portion would not start until the whole set of data acquisition and parallel resorting procedures are completed and then followed by backprojection for image reconstruction. FDKHSCW possess the advantage that once a 2-D projection data is acquired, the filtering portion can start and be immediately followed by backprojection. As long as the gantry speed and readout rate is high enough, this scheme can provide almost real time monitoring when continuous dynamic imaging is conducted. Wang (G. Wang, "X-ray micro-CT with a displaced detector array," *Med. Phys.* 29, 1634-1636 (2002)) developed a weighting scheme for cone beam full circular scan reconstruction on a displaced detector array without rebinning the projection data for reconstruction. As for the redundant area, our scheme can be applied to this algorithm by adjusting the weighting conditions in the scanning range.

Recently, a new circular 3-D weighting reconstruction algorithm was proposed to reduce cone beam artifacts based on the investigation on the data inconsistency between a direct ray and its conjugate rays. The basic idea is to have filtered projection data multiplied by correction coefficients that are cone beam geometrically dependent during the backprojection. But the artifact it corrects is not what FDKHSCW tries to correct here, namely attenuation coefficient drop. However, the two schemes can be combined.

In conclusion, by incorporating a new cone beam weighting scheme, a new FDK-based heuristic half-scan approximate algorithm for circular trajectory has been proposed based on a flat panel detector, and the numerical simulation demonstrated its feasibility.

Because both the scanning and the processing of the data can be accomplished in less time, imaging can be accomplished much faster. Thus, scanning in four dimensions (three dimensions of space and one of time) becomes possible.

Related systems and methods are disclosed in the following U.S. patents: U.S. Pat. No. 6,987,831, "Apparatus and method for cone beam volume computed tomography breast imaging"; U.S. Pat. No. 6,618,466, "Apparatus and method for x-ray scatter reduction and correction for fan beam CT and cone beam volume CT"; U.S. Pat. No. 6,504,892, "System and method for cone beam volume computed tomography using circle-plus-multiple-arc orbit"; U.S. Pat. No. 6,480,565 "Apparatus and method for cone beam volume computed tomography breast imaging"; U.S. Pat. No. 6,477,221, "System and method for fast parallel cone-beam reconstruction using one or more microprocessors"; U.S. Pat. No. 6,298,110, "Cone beam volume CT angiography imaging system and method": U.S. Pat. No. 6,075,836, "Method of and system for intravenous volume tomographic digital angiography imaging"; and U.S. Pat. No. 5,999,587, "Method of and system for cone-beam tomography reconstruction," whose disclosures are all incorporated by reference in their entireties into the present disclosure. The techniques disclosed in those patents can be used in conjunction with the techniques disclosed herein.

BRIEF DESCRIPTION OF THE DRAWINGS

Preferred embodiments of the present invention will be set forth in detail with reference to the drawings, in which.

DETAILED DESCRIPTION OF THE PREFERRED EMBODIMENTS

Figure 1:
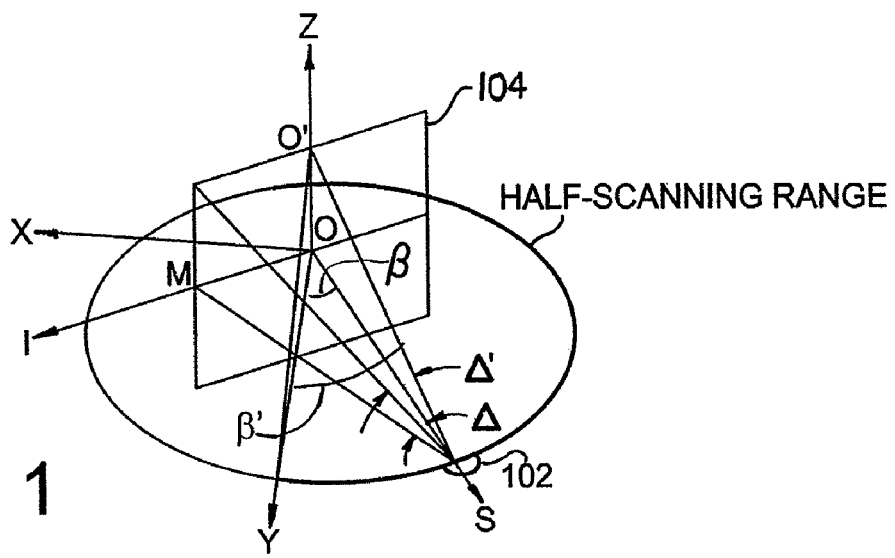
FIG. 1 shows a scan geometry for the first preferred embodiment.

Preferred embodiments of the invention will be set forth in detail with reference to the drawings, in which like reference numerals refer to like elements or steps throughout.

The FDK algorithm expands upon the fan beam algorithm by summing the contribution to the object of all the tilted fan beams. The reconstruction is based on filtering and back projecting a single fan beam within the cone. Based on the cone beam geometry in FIG. 1, which shows the relative locations of the cone beam emitter or other x-ray source 102 and the plane of the flat-panel detector 104, the formula of the FDK is:

$$f(x, y, z) = \frac{1}{2} \int_0^{2\pi} \frac{so^2}{(so-s)^2} \cdot \left\{ \left[ R_\beta(np, m\xi) \frac{so}{\sqrt{so^2 + m^2\xi^2 + n^2 p^2}} \right] * h(np) \right\} d\beta \quad (1)$$

$$s = -x\sin\beta + y\cos\beta;$$

The * sign denotes the convolution; so: the distance from the x-ray source to the origin; n,m: integer value where n=0 and m=0 corresponds to the central ray passing through the origin; β: the projection angle defined in the scanning plane; p: the virtual detector sampling interval along the t axis; ξ: the virtual detector sampling interval along the Z axis; $R_\beta$(np, mξ): the actual discrete 2-D projection data; h(np): the discrete one-dimensional ramp filter impulse response along the t axis.

The pre-weight term, $$\frac{so}{\sqrt{so^2 + m^2\xi^2 + n^2 p^2}},$$

can be factorized into two cosine terms as $$\frac{\sqrt{so^2 + n^2 p^2}}{\sqrt{so^2 + m^2\xi^2 + n^2 p^2}} \frac{so}{\sqrt{so^2 + n^2 p^2}}.$$

This means that FDK projects the off-scanning plane projection data into the scanning plane and then follows the 2-D fan beam reconstruction algorithm. In equation (1), the factor of ½ in front of the integral is used to cancel the projection redundancy when a full circular scanning is conducted. This implies that the off-scanning plane projection data has the same redundancy as the projection data in the scanning plane.

The cone beam half-scan scheme is also the extension of the fan beam half-scan combined with the FDK, in which the weighting coefficients calculated from the scanning plane geometry are applied to all projection rows as follow, $$f(x, y, z) = \int_0^{\pi+2\Delta} \frac{so^2}{(so-s)^2} \cdot \left\{ \left[ \omega(\beta, np) \cdot R_\beta(np, m\xi) \cdot \frac{so}{\sqrt{so^2 + m^2\xi^2 + n^2p^2}} \right] * h(np) \right\} d\beta \quad (2)$$

$$s = -x\sin\beta + y\cos\beta;$$

This is the FDKHSFW scheme, where $\Delta$ is half the full fan angle of the central scanning plane along the t axis. The off-scanning plane projection data are still treated as they have the same redundancy. $\omega(\beta, np)$ is the discrete weighting coefficient, calculated based on the scanning plane geometry, and can be represented by Parker's weighting function or any other weighting function as long as it can make a smooth transition between the doubly and singly sampled regions to avoid discontinuities at the borders of these regions. Undoubtedly, FDKHSFW holds all the properties that the FDK full scan scheme does.

For cone beam projection data off the scanning plane, however, it is impossible to obtain completely doubly sampled projections for a single circular orbit acquisition, even if projections are sampled over 360°. In other words, the projection redundancy becomes less and less when projection rows get further away from the scanning plane. If the FDK algorithm had been directly applied to un-weighted half-scan projection data, the reconstructed images would unavoidably have artifacts. One way to handle the weighting on the less redundancy projection row data away from scanning plane, is proposed as follows:

$$\omega(\beta', np) = \begin{cases} \sin^2\left(\frac{\pi}{4} \frac{\beta'}{\Delta' - \tan^{-1}\left(\frac{np}{so'}\right)}\right), & 0 \le \beta' \le 2\Delta' - 2\tan^{-1}\left(\frac{np}{so'}\right) \\ 1, & 2\Delta' - 2\tan^{-1}\left(\frac{np}{so'}\right) \le \beta' \le \pi - 2\tan^{-1}\left(\frac{np}{so'}\right) \\ \sin^2\left(\frac{\pi}{4} \frac{\pi + 2\Delta' - \beta'}{\Delta' + \tan^{-1}\left(\frac{np}{so'}\right)}\right), & \pi - 2\tan^{-1}\left(\frac{np}{so'}\right) \le \beta' \le \pi + 2\Delta' \end{cases} \quad (3)$$

where $$\beta' = \beta \cdot \frac{1}{\sqrt{1 + m^2\xi^2/so^2}}$$

$$so' = \sqrt{so^2 + m^2\xi^2}$$

$$\Delta' = \tan^{-1}\left(\frac{MO}{so'}\right);$$

$\beta'$ is the cone-weighting angle and is defined between the two lines O'S and OY when the cone-shaped curve plane O'SY is flattened. $\beta'$ is dependent on the position of the row projection data in the Z direction (rotation axis). $\Delta'$ is half of the titled fan angle that is adopted from G. T. Gullberg and G. L. Zeng, "A cone-beam filter backprojection reconstruction algorithm for cardiac single photon emission computed tomography," *IEEE Trans. Med. Imaging* 11, 91-101 (1992). Notice that when m is zero, this weighting function is actually the Parker's weighting function for fan-beam.

By incorporating the cone-beam weighting function with the FDK, the FDKHSCW is obtained as follows:

$$f(x, y, z) = \int_0^{\pi+2\Delta} \frac{so^2}{(so-s)^2} \cdot \left\{ \left[ \omega(\beta', np) \cdot R_\beta(np, m\xi) \cdot \frac{so}{\sqrt{so^2 + m^2\xi^2 + n^2p^2}} \right] * h(np) \right\} d\beta \quad (4)$$

$$s = -x\sin\beta + y\cos\beta;$$

Please note that the projection data must be weighted prior to being filtered. Since FDKHSFW is the commonly acknowledged scheme for half-scan reconstruction, the requirement for FDKHSCW is that it should produce no more artifacts than FDKHSFW.

Figure 2:
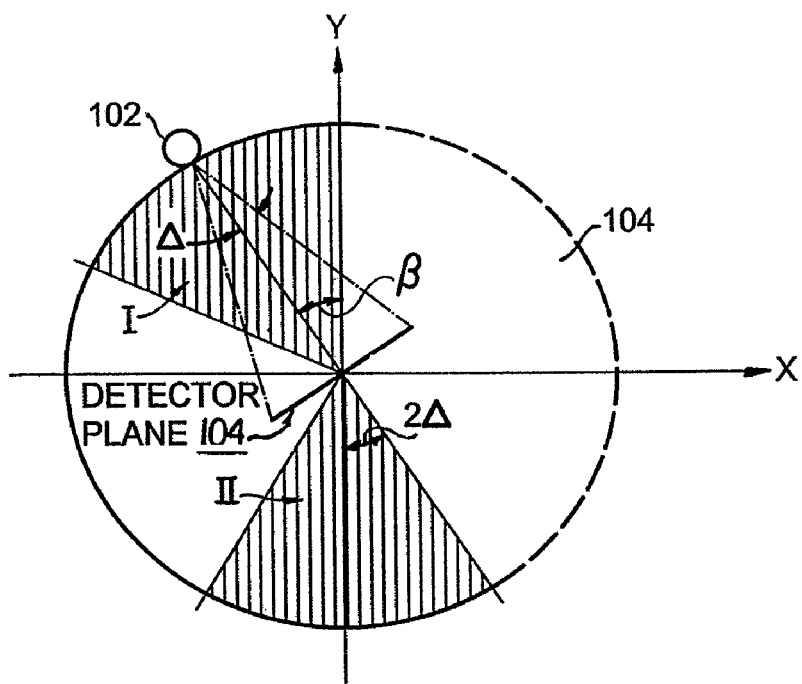
FIG. 2 shows redundant regions in the scan geometry of FIG. 1.
Figure 3A:
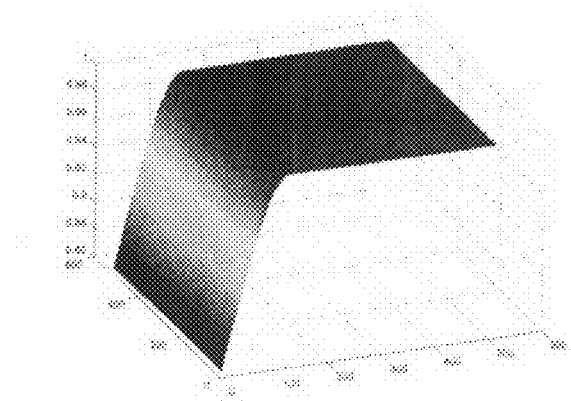
FIGS. 3A-3D show weighting coefficients.
Figure 3B:
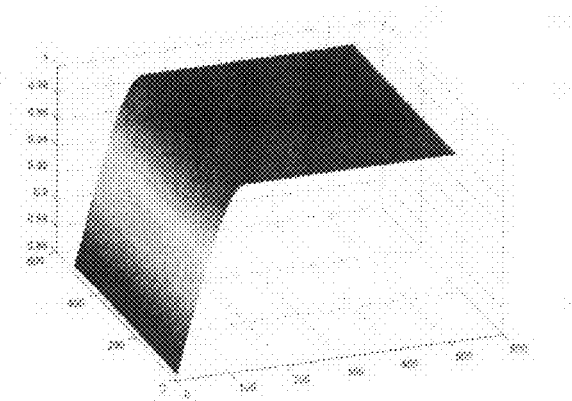
Figure 3C:
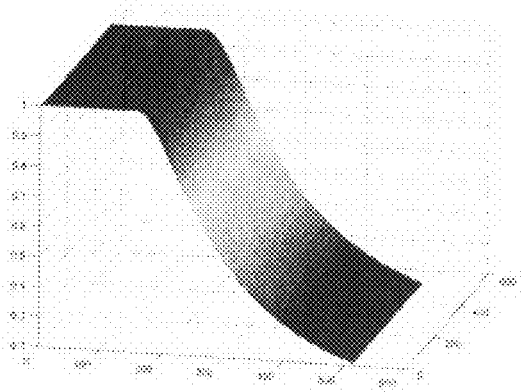
Figure 3D:
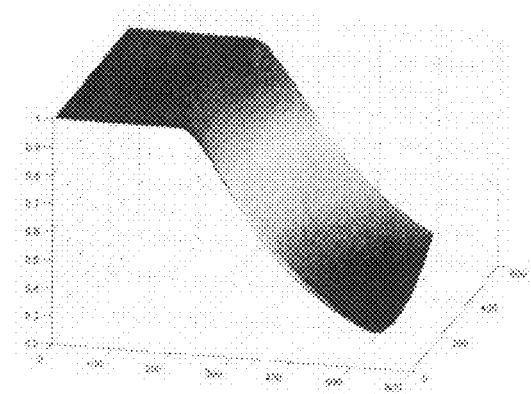

Further investigation of half scan cone beam weighting will now be disclosed. In a circular fan-beam half-scan, there are two redundant regions in the scanning plane in terms of the projection angle $\beta$. FIG. 2 shows that the projecting ray data acquired in region I will have a conjugate ray data in region II. In these two regions, the projection ray data is wholly or partly redundant. If half of the full fan angle is $\Delta$ degrees, the half scan range in terms of projection angle defined in the scanning plane is from 0° to 180°+2$\Delta$. The first and second redundant region is from 0° to 4$\Delta$ and from 180°-2$\Delta$ to 180°+2$\Delta$ respectively. In the traditional FDK cone-beam half scan scheme, all the row projection data are weighted by the same set of coefficients defined in the scanning plane because the row projection data away from the scanning plane are expected to have the same redundancy as those in the scanning plane.

The proposal of the circular cone-beam half scan weighting scheme is based on the idea that the weighting coefficients should be different for projection data in different rows, and for the row projection data furthest away from the scanning plane, it should be weighted less. As of this date, we have not seen any literature discussing this issue. We found that if we use $$\beta' = \beta \frac{1}{\sqrt{1 + m^2\xi^2/so^2}}$$

as the weighting angle for different row projection data, then, the weighting coefficients in the first redundant region away from the scanning plane are not much different from those calculated in the scanning plane; the biggest difference is below 0.2 percent if $\Delta=15°$ and the half cone angle is also 15°. On the other hand, when $\beta'$ is used as the weighting angle in the second redundant region, the weighting coefficients away from the scanning plane behave obviously differently from those in the scanning plane and different from each other at the different rows, thus resulting in the compensation for the density drop in the place away from the scanning plane in the reconstruction image. The weighting angle $\beta'$ has two characteristics: first, it has row position dependence that is reflected by m$\xi$, indirectly connected to the cone angle information; second, it has less difference from $\beta$ when $\beta$ is in the first redundant region than when $\beta$ is in the second redundant region. Thus, it is beneficial to construct the cone angle dependent weighting coefficients in the second redundant region to achieve our scheme.

In order to make computer simulation closer to the practical CBCT configuration, geometric parameters are set in terms of physical length (millimeter) rather than normalized units. The distances from the X-ray source to the iso-center of the reconstruction and to the detector are 780 mm, and 1109 mm respectively. The full fan and cone angle are 30 degrees. The detector area is 595×595 mm² and has a 512 by 512 matrix size. The voxel size is 0.816 mm³. Cartesian coordinate (X, Y, Z) is used to define the object, where Z is the rotation axis. The sampling rate of projection angle is 0.8° with the total number of projection images of 450 for full scan and 262 for half scan. The low contrast Shepp-Logan phantom was used (see Ref. 7 for geometrical parameters), all of its geometrical parameters are multiplied by 200 to simulate the physical length (millimeter) of the phantom.

Based on the scanning geometrical parameters defined above weighting coefficient distribution associated with FDKHSFW and FDKHSCW are compared by picking up $\beta=46°$ in the redundant region I and $\beta=192°$ in the redundant region II. FIGS. 3A-3D show, respectively, FDKHSFW ($\beta=46°$), FDKHSCW ($\beta=46°$), FDKHSFW ($\beta=192°$) and FDKHSCW ($\beta=192°$).

Figure 4A:
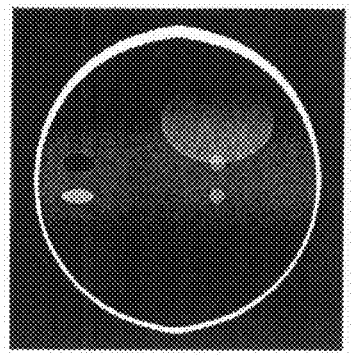
FIGS. 4A-4C show reconstructed sagittal images from a phantom.
Figure 4B:
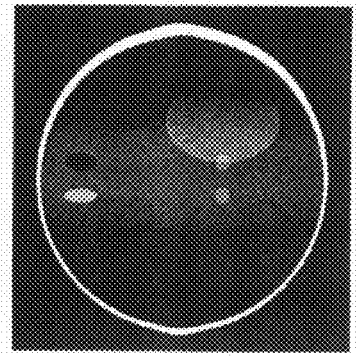
Figure 4C:
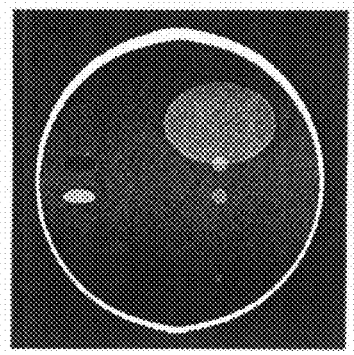
Figure 4D:
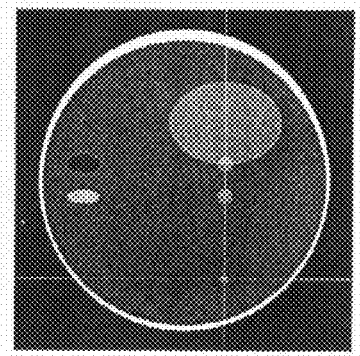
FIG. 4D shows the phantom.
Figure 4E:
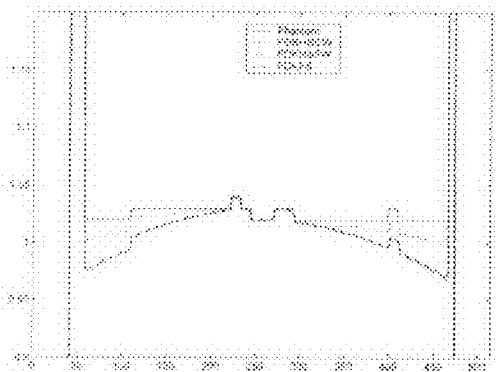
FIGS. 4E and 4F show line profile comparisons from the images in FIGS. 4A-4C along the lines shown in FIG. 4D.
Figure 4F:
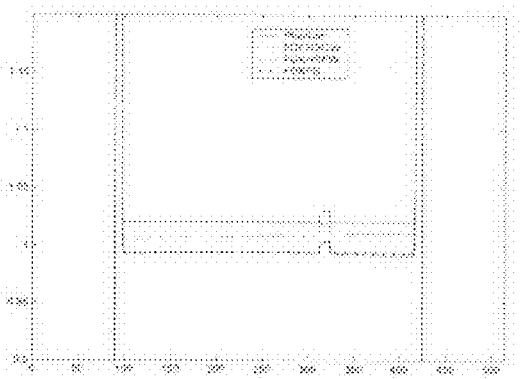

FIGS. 4A-4C show the reconstructed sagittal image from different FDK schemes (respectively, FDKFS, FDKHSFW and FDKHSCW) at X=0 mm with the display window [1.005 1.05]. FIG. 4D shows the phantom. FIGS. 4E and 4F show the profile comparison along the solid white vertical and horizontal lines in the phantom image of FIG. 4D. The ramp filter was used on the noise-free weighted projection data before back-projection.

In order to test the performance of this new scheme over the quantum noise that is commonly encountered in practical CBCT data acquisition, we generated quantum noise contaminated data. X-ray with 100 kVp was selected which corresponds to an effective photon fluence of 2.9972*10⁷ photons/cm²·mR. The exposure level per projection was set to 4 mR, the total exposure levels for FDKFS and FDKHSCW are 1800 mR and 1048 mR respectively.

Figure 5A:
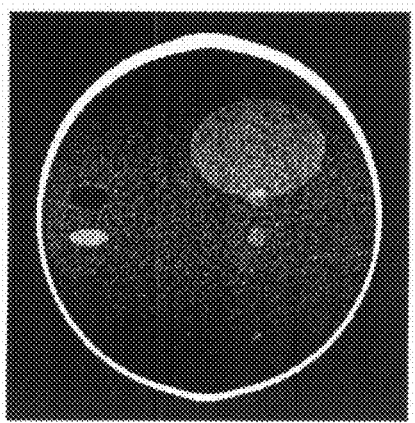
FIGS. 5A and 5B show results with different noise levels.
Figure 5B:
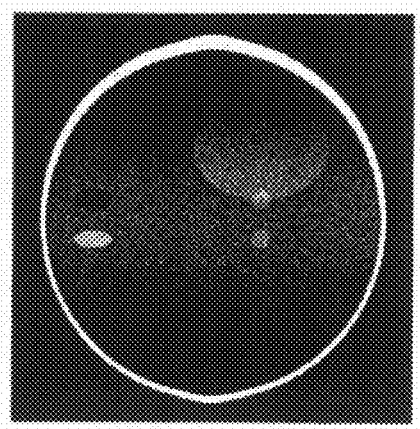
Figure 5C:
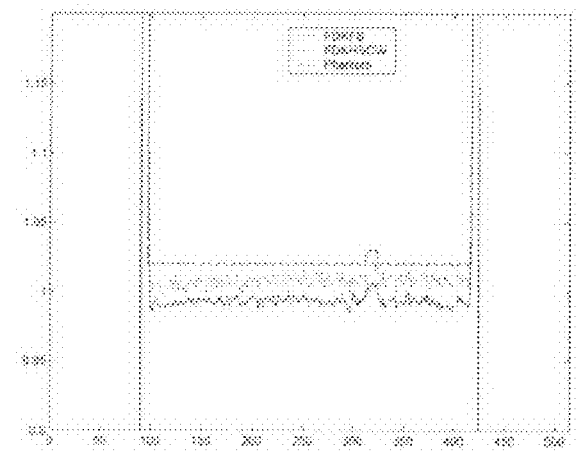
FIGS. 5C and 5D show profile comparisons from the results of FIGS. 5A and 5B.
Figure 5D:
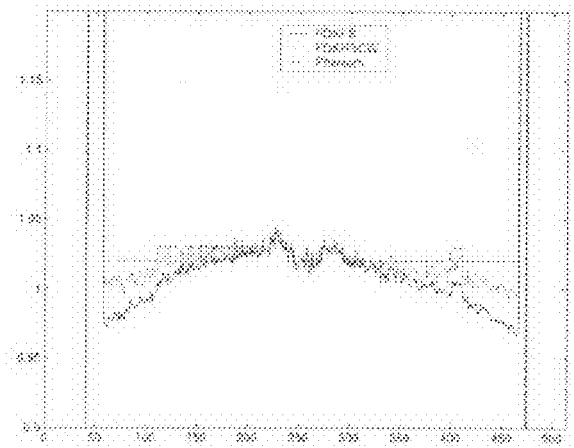

FIGS. 5A-5D show the reconstructed results under different noise levels and profile comparisons. A Hamming window is used during filtering to suppress the noise. More specifically, FIGS. 5A and 5B show, respectively, FDKFS with total exposure level of 1800 mR and FDKHSCW with total exposure level of 1048 mR, while FIGS. 5C and 5D show a profile comparison between FDKFS, FDKHSCW, and the phantom along the solid vertical and horizontal lines in FIG. 4D.

Figure 6:
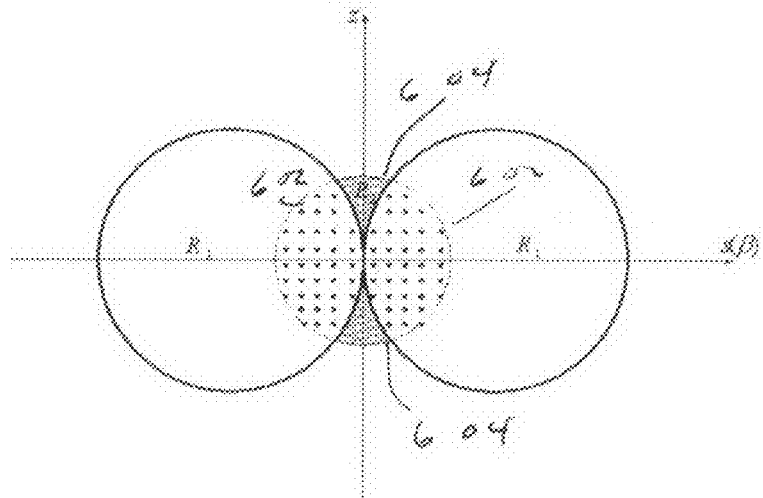
FIG. 6 shows the Radon domain in a second preferred embodiment.

A variation of the first preferred embodiment will be presented. In terms of the Radon domain, as FIG. 6 shows, the dotted points in the circle (zones 602) represent the radon value of the object acquired in a circular scan, while the shaded area in the circle (zone 604) represents the missing radon points set which cannot be acquired through a circular scan. As argued by Hu, in a circular scan, FDK uses only the redundant points inside the object circle and on the dotted arc boundaries, but does not use the non-redundant points on the solid arc boundaries within the object circle. Thus, the following correction term is used:

$$f_2(t, s, z) = -\frac{1}{\pi + 2\Delta} \int_0^{\pi+2\Delta} \frac{z}{(so-s)^2} P_\beta(z') d\beta$$

where $s = -x\sin\beta + y\cos\beta$ $t = x\cos\beta + y\sin\beta$ $z' = \frac{so+z}{so-s}$ -continued $$P_\beta(z) = \frac{1}{2\pi} \frac{\partial \sigma_\beta(z)}{\partial z}$$

$$\sigma_\beta(z) = \int R_\beta(t, z) \cdot \frac{so}{\sqrt{so^2 + \xi^2 + p^2}} dt.$$

If the above reconstruction is designated $f_1(t, s, z)$, then the final reconstruction is $$f(t,s,z)=f_1(t,s,z)+f_2(t,s,z)$$

A second preferred embodiment, which is particularly applicable to breast imaging, will now be disclosed.

Figure 7A:
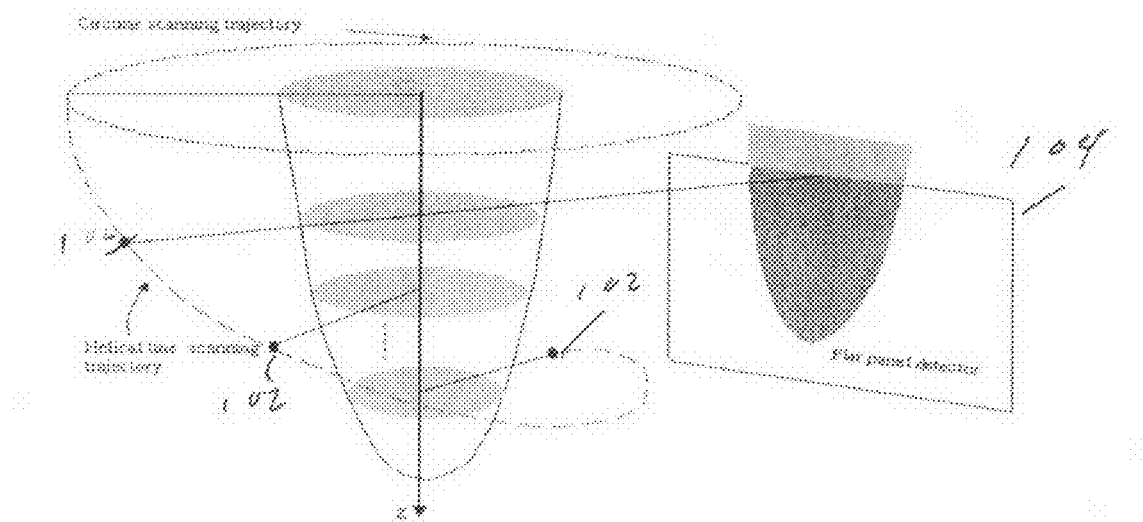
FIGS. 7A and 7B show a scan geometry in the second preferred embodiment.
Figure 7B:
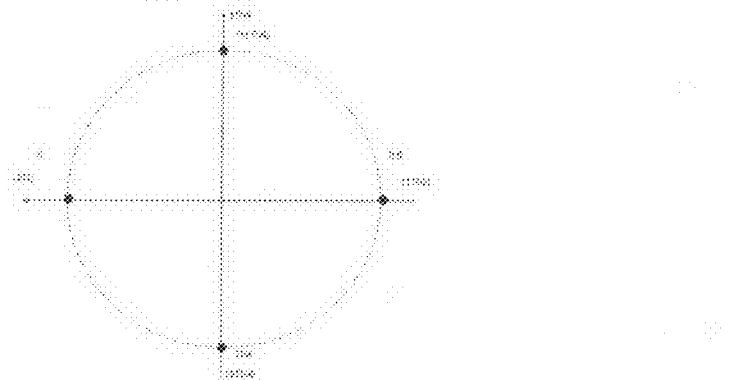

Based on the geometric parameters of current CBBCT, we designed a new scanning scheme for CBBCT. As FIGS. 7A and 7B show, the position of the x-ray source 102 is at z=0 cm during the circular scan. After the circular scan, the x-ray source 102 and detector 104 lower down simultaneously while they are still rotating. When the x-ray source gets to the point where z=10, it starts to shoot and keeps shooting between the interval $\Delta l$ till it finishes eight shoots in this helical scan. For each shoot during the helical scan, the x-ray source still maintains the same collimation as it does in circular scan. This scheme is called sparse spiral scan. In practice, to efficiently implement sparse spiral scan, the system is required to comprises a slip ring on the gantry frame for providing the connection to the electrical power to the on-gantry components and the communication between the two-dimensional detector and the computer system and a motor to move the gantry or the support of the object on which the object rests up or down along the rotation axis;

The projection angles associated with helical line scan are illustrated by FIG. 7B. There are eight shoot points during helical scan which cover the angular range of 4 $\pi$, and the movement in Z direction is from 48 mm to 128 mm with the increment interval of 10 mm based on the size of the simulated breast phantom.

Some of the radon data points acquired from this additional scanning trajectory still can be acquired through the circular scan; this is what is called redundancy sampling points in radon domain, and can be efficiently eliminated by the redundant window function (RWF), and the geometric setup of the collimator as during the HL scanning can avoid the redundant sampling radon points between those shooting points on this helical line. Since the collimation during helical line scanning unavoidably induces the longitudinal truncation, a geometric dependent truncation window function (TWF) will be used to handle this case.

Composite reconstruction framework is probably the most preferable algorithm for the CBCTBI. The reconstructed object is $f(\bar{r})$, and can be mathematically described by the following equation:

$$f(\bar{r})=f_1(\bar{r})+f_2(\bar{r})+f_{HL}(\bar{r})$$

where $f_1(\bar{r})$: reconstructed object from single circular scan, $f_2(\bar{r})$: reconstructed object from Hui's term based on single circular scan, $f_{HL}(\bar{r})$: reconstructed object from sparse helical line scan [5], Based on FIG. 7A, the mathematic formula of the $f_1(\bar{r})$, and $f_2(\bar{r})$ can be described as $$f_1(\vec{r}) = \frac{1}{4\pi^2} \oint \frac{d^2}{(d+\vec{r}\cdot\vec{s})^2} P_1(Y,Z) d\beta$$

where $$P_1(t, Z_0) = \int \frac{d}{\sqrt{d^2+t'^2+Z^2}} P_\beta(t, Z_0) h(t-t') dt'$$

$$Y = d\frac{\vec{r}\cdot t}{d+\vec{r}\cdot\vec{s}},$$

$$Z = d\frac{z}{d+\vec{r}\cdot\vec{s}},$$

$$f_2(\vec{r}) = -\frac{1}{4\pi^2} \oint \frac{z}{(d+\vec{r}\cdot\vec{s})^2} P_2(Z) d\beta$$

where $$P_2(Z) = \frac{\partial}{\partial Z} \int \frac{d}{\sqrt{d^2+t^2+Z^2}} P_\beta(t, Z) dt$$

$$Z = d\frac{z}{d+\vec{r}\cdot\vec{s}},$$

The reconstruction term for the helical line scan cab be formatted as a type of filtered backprojection (FBP):

$$f_{hl}(\vec{r}) = -\frac{1}{4\pi^2} \int d\beta \int_{Z_0}^{Z_n} \Delta Z \int_{-\pi/2}^{\pi/2} H_{Z_i}(l,\varphi) d\varphi$$

$$H_{Z_i}(l,\varphi) = |\cos\varphi| \frac{d^2+l^2}{d^2} w_{Z_i}(l,\varphi) w_{d_{Z_i}}(l,\varphi) \begin{pmatrix} \frac{2l}{d^2} \frac{\partial \sum_{Z_i}(l,\varphi)}{\partial l} + \\ \frac{d^2+l^2}{d^2} \frac{\partial^2 \sum_{Z_i}(l,\varphi)}{\partial l^2} \end{pmatrix}$$

$$\sum\nolimits_{Z_i}(l,\varphi) = \int\int \frac{d}{\sqrt{d^2+t^2+Z^2}} P_{Z_i}(t,Z) \delta(t\sin\varphi + Z\cos\varphi - l) dt dZ$$

$$w_{Z_i}(l,\varphi) = \begin{cases} 1, & 2lZ_i\cos\varphi + Z_i^2\cos^2\varphi - d^2\sin^2\varphi > 0 \\ 0, & \text{otherwise} \end{cases}$$

$$w_{d_{Z_i}}(l,\varphi) = \begin{cases} 1, & \text{line } c_1c_2 \text{ not get in the region of } \Sigma \\ 0, & \text{line } c_1c_2 \text{ get in the region of } \Sigma \end{cases}$$

$w_{z_i}(l, \phi)$ is the window function used to block out the radon data acquired through helical line scan but have already been accessed by circular scan. Based on the scanning design, the helical line scan will unavoidably encounter the longitudinal truncation during the scanning. Some radon points it acquires do not reflect the actual radon data and should be eradicated during the back-projection. Window $W_{d_{z_i}}(l, \phi)$ is used to accomplish this purpose.

While preferred embodiments and variations thereon have been disclosed above, those skilled in the art who have reviewed the present disclosure will readily appreciate that other embodiments can be realized within the scope of the invention. For example, numerical values are illustrative rather than limiting. Also, the invention can be implemented on any suitable scanning device, including any suitable combination of a beam emitter, a flat panel or other two-dimensional detector or other suitable detector, and a gantry for relative movement of the two, as well as a computer for processing the image data to produce images and a suitable output (e.g., display or printer) or storage medium for the images. Software to perform the invention may be supplied in any suitable format over any medium, e.g., a physical medium such as a CD-ROM or a connection over the Internet or an intranet. Therefore, the present invention should be construed as limited only by the appended claims.

We claim:

1. A method for forming an image of an object, the method comprising:
    (a) performing a cone-beam scan of the object in a scanning plane by using a cone-beam emitter and a detector to perform a half-circle scanning geometry so as to obtain projection data for a plurality of rows;
    (b) weighting the projection data with a weighting factor to produce weighted projection data, wherein the weighting factor decreases as the rows become farther from the scanning plane, wherein the weighting factor is a function of a weighting angle which is a function of the row and a scan angle, wherein the weighting angle is $$\beta' = \beta \frac{1}{\sqrt{1+m^2\xi^2/so^2}}$$

where $\beta$ is the scan angle, m is a number of the row, $\xi$ is a virtual detector sampling interval of the detector, and so is a distance from the emitter to an origin of the scanning geometry; and
    (c) forming the image from the weighted projection data.

2. The method of claim 1, wherein step (c) comprises filtering the weighted projection data.

3. The method of claim 1, wherein the weighting factor is $$\omega(\beta', np) = \begin{cases} \sin^2\left(\frac{\pi}{4} \frac{\beta'}{\Delta' - \tan^{-1}\left(\frac{np}{so'}\right)}\right), & 0 \leq \beta' \leq 2\Delta' - 2\tan^{-1}\left(\frac{np}{so'}\right) \\ 1, & 2\Delta' - 2\tan^{-1}\left(\frac{np}{so'}\right) \leq \beta' \leq \pi - 2\tan^{-1}\left(\frac{np}{so'}\right) \\ \sin^2\left(\frac{\pi}{4} \frac{\pi+2\Delta'-\beta'}{\Delta' + \tan^{-1}\left(\frac{np}{so'}\right)}\right), & \pi - 2\tan^{-1}\left(\frac{np}{so'}\right) \leq \beta' \leq \pi + 2\Delta' \end{cases}$$

where n is a column number, p is a virtual detector sampling interval along a t axis, $$so' = \sqrt{so^2 + m^2\xi^2};$$

$$\Delta' = \tan^{-1}\left(\frac{MO}{so'}\right); \text{ and}$$

MO is a half-width of the detector.

4. The method of claim 1, further comprising, between steps (b) and (c), adding to the weighted projection data a correction term representing information in Radon space which cannot be acquired through a circular scan.

5. The method of claim 1, wherein steps (a), (b) and (c) are performed in real time.

6. A system for forming an image of an object, the system comprising:
   a cone-beam emitter;
   a detector;
   a gantry for causing relative movement of the emitter and the detector for performing a cone-beam scan of the object in a scanning plane by using a cone-beam emitter and a detector to perform a half-circle scanning geometry so as to obtain projection data for a plurality of rows; and
   a processor, receiving the projection data, for weighting the projection data with a weighting factor to produce weighted projection data, wherein the weighting factor decreases as the rows become farther from the scanning plane and forming the image from the weighted projection data, wherein the weighting factor is a function of a weighting angle which is a function of the row and a scan angle, wherein the weighting angle is $$\beta' = \beta \frac{1}{\sqrt{1 + m^2 \xi^2 / so^2}}$$

where $\beta$ is the scan angle, m is a number of the row, $\xi$ is a virtual detector sampling interval of the detector, and so is a distance from the emitter to an origin of the scanning geometry.

7. The system of claim 6, wherein the processor filters the weighted projection data.

8. The system of claim 6, wherein the weighting factor is $$\omega(\beta', np) = \begin{cases} \sin^2\left(\frac{\pi}{4} \frac{\beta'}{\Delta' - \tan^{-1}\left(\frac{np}{so'}\right)}\right), & 0 \leq \beta' \leq 2\Delta' - 2\tan^{-1}\left(\frac{np}{so'}\right) \\ 1, & 2\Delta' - 2\tan^{-1}\left(\frac{np}{so'}\right) \leq \beta' \leq \pi - 2\tan^{-1}\left(\frac{np}{so'}\right) \\ \sin^2\left(\frac{\pi}{4} \frac{\pi + 2\Delta' - \beta'}{\Delta' + \tan^{-1}\left(\frac{np}{so'}\right)}\right), & \pi - 2\tan^{-1}\left(\frac{np}{so'}\right) \leq \beta' \leq \pi + 2\Delta' \end{cases}$$

where n is a column number, p is a virtual detector sampling interval along a t axis, $$so' = \sqrt{so^2 + m^2 \xi^2};$$

$$\Delta' = \tan^{-1}\left(\frac{MO}{so'}\right); \text{ and}$$

MO is a half-width of the detector.

9. The system of claim 6, wherein the processor adds to the weighted projection data a correction term representing information in Radon space which cannot be acquired through a circular scan.

10. The system of claim 6, wherein the emitter, detector, gantry and processor operate in real time.

* * * * *